US006180755B1

(12) United States Patent
Brimmer et al.

(10) Patent No.: US 6,180,755 B1
(45) Date of Patent: Jan. 30, 2001

(54) PROCESS FOR SEPARATING ORGANIC MONOMERS OR AUXILIARIES

(75) Inventors: Joachim Brimmer, Achim; Wolfgang Sirtl, Bremen, both of (DE)

(73) Assignee: Joachim Brimmer Ingenieurburo Anlagenbau GmbH, Achim (DE)

( * ) Notice: Under 35 U.S.C. 154(b), the term of this patent shall be extended for 0 days.

(21) Appl. No.: 09/171,494

(22) PCT Filed: Mar. 25, 1997

(86) PCT No.: PCT/EP97/01498

§ 371 Date: Oct. 20, 1998

§ 102(e) Date: Oct. 20, 1998

(87) PCT Pub. No.: WO97/40081

PCT Pub. Date: Oct. 30, 1997

(30) Foreign Application Priority Data

Apr. 23, 1996 (DE) ............................................. 196 16 046

(51) Int. Cl.$^7$ ..................................................... C08G 18/10
(52) U.S. Cl. ......................... 528/483; 528/490; 528/503; 528/903
(58) Field of Search ............................... 526/77; 528/483, 528/503, 490, 903

(56) References Cited

U.S. PATENT DOCUMENTS

| 4,306,058 | 12/1981 | Copelin | 528/498 |
| 4,902,780 | * 2/1990 | Bourrain et al. | 528/483 |
| 5,237,048 | * 8/1993 | Miyakawa et al. | 528/483 |

FOREIGN PATENT DOCUMENTS

| 3323940 | 1/1985 | (DE) . |
| 4136539 | 5/1992 | (DE) . |
| 0337898 | 10/1989 | (EP) . |
| 0374879 | 6/1990 | (EP) . |

* cited by examiner

*Primary Examiner*—Fred Teskin
(74) *Attorney, Agent, or Firm*—Baker Botts L.L.P.

(57) ABSTRACT

The invention consists of a process for separating organic monomers or auxiliaries, which are used in synthesizing organic polymers or take part in the polymerization reaction, from the prepolymer resulting from the synthesis, in which the monomers or auxiliaries are extracted from the prepolymer by means of compressed and dried carbon dioxide as solvent.

18 Claims, 1 Drawing Sheet

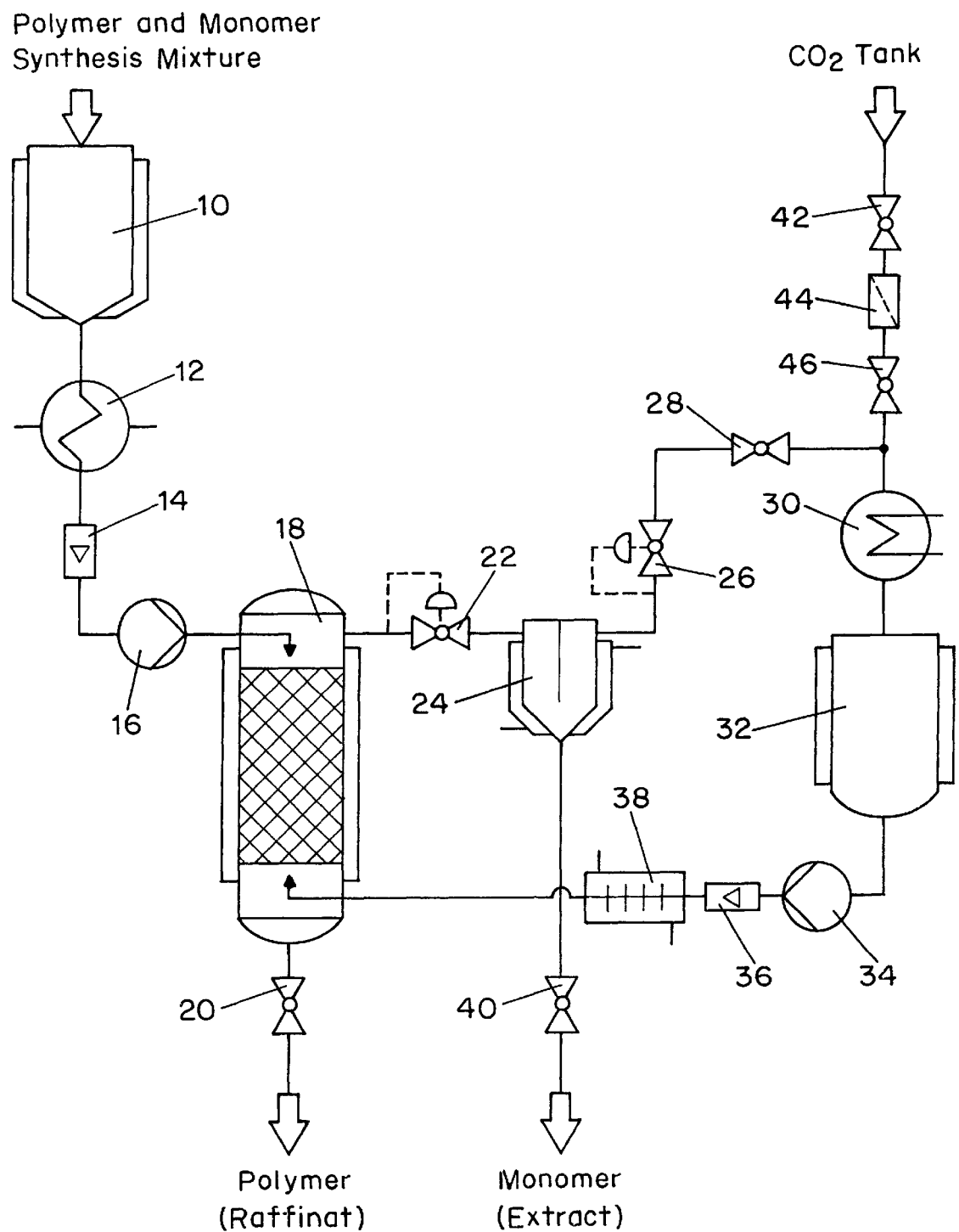

PROCESS FOR SEPARATING ORGANIC MONOMERS OR AUXILIARIES

The invention relates to a process for separating organic monomers or auxiliaries which are used in synthesizing organic polymers or take part in the polymerization reaction, whereby the monomers or auxiliaries are extracted from the prepolymer obtained by the synthesis by means of compressed carbon dioxide as solvent and whereby the carbon dioxide is used in its thermo-dynamic state above its critical pressure and above its critical temperature.

Such a process, which serves to remove the monomers used in the synthesis, which are present in excess or are thermally unconverted, as well as the additives, such as solvents, diluents, stabilizers, starters or the like, used in the synthesis as auxiliaries, from the prepolymer, is disclosed in U.S. Pat. No. 4,871,460. There, the carbon dioxide is introduced in a moist and supercritical state. The monomers or auxiliaries separated in this way are recovered with a relatively high proportion of moisture and therefore are unsuitable for further use, for example for return to the production process.

German Patents DE 3,836,093, DE 4,136,490 and DE 4,232,015, as well as German Letters of Disclosure DE 2,414,391 A1 and European Patents 0,464,483 and 0,340,584, likewise disclose a variety of processes for separating monomers and/or polymers. In these known processes additional auxiliaries, which for example react with the monomers to be neutralized in the prepolymer, are added to the prepolymer for neutralizing. Consequently, neutralizing involves a chemical process in which the reaction product of monomers, [with] the auxiliaries added for neutralizing, remains in the prepolymer. Another common disadvantage of the known processes is that the separated monomers are impure and hence unsuitable for purposes of further synthesis and therefore must be disposed of at high cost.

The object of the invention is to refine the process of the type mentioned at the beginning in such a way that the monomers or auxiliaries are recovered essentially moisture-free, so that further use of the monomers, in particular return of the monomers directly to the production process, is possible.

According to the invention, this object is accomplished by a process for separating organic monomers or auxiliaries which are used in synthesizing organic polymers or take part in the polymerization reaction, whereby the monomers or auxiliaries are extracted from the prepolymer obtained by the synthesis by means of compressed carbon dioxide as solvent, and whereby the carbon dioxide is used in its thermodynamic state above its critical pressure and above its critical temperature. The process according to the invention is characterized in that the carbon dioxide is dried to a moisture content under 20 ppm before it is brought together with the prepolymer.

The process according to the invention allows the residual monomer content in the purified prepolymer to be reduced to values under 0.1%, so that in further processing of the purified prepolymers, for example, no special protective measures are necessary on account of the monomers contained. In addition, because of the use of dry $CO_2$ the separated monomers accumulate with a high purity of up to 99.8%, for example, hence can be used for the synthesis again and need not be disposed of in onerous fashion. The dry carbon dioxide may alternatively be returned for further extraction. This permits a closed extraction circuit in which no emissions are released. Nor need any additional chemicals be used. Added to this is the fact that the protective-gas effect of carbon dioxide may also be utilized in, in particular, containerizing the purified prepolymer. Deterioration of the prepolymer due to oxygen or moisture may be prevented in simple fashion. Overall, considerably improved product quality is obtained, with simultaneous and complete recycling of the raw materials used, monomers or auxiliaries.

For extraction, the compressed and dried carbon dioxide is brought into contact with the prepolymer. Then, the monomers or auxiliaries are dissolved out of the prepolymer by the carbon dioxide and dissolve in the carbon dioxide. In this way, the content of monomers or auxiliaries in the prepolymer is reduced.

The process of high-pressure carbon dioxide extraction for recovering extracts of natural products is already well known (German patent Nos. DE 2,127,618, DE 2,127,611 and DE 4,335,321). However, on the basis of the experience gained in these applications of high-pressure carbon dioxide extraction, the process for separating organic monomers or auxiliaries, which are used in synthesizing organic polymers or take part in the polymerization reaction, from the prepolymer seemed unsuitable for synthesis. Namely, the previous applications showed that carbon dioxide is a suitable solvent for lipophilic substances, while hydrophilic polar substances or substance classes are insoluble in carbon dioxide.

This is clearly apparent in the example of hops extraction: The lipophilic constituents are recovered as total extract by means of high-pressure carbon dioxide extraction, while the hydrophilic polar substances (cellulose, sugar, starch) remain as residue. The extract or mixture thus obtained, consisting of a multiplicity of lipophilic substances/substance classes (e.g., a-acids, b-acids, hops oils, aromatic substances, etc.), cannot be further broken down into the individual substances or components or separated into fractions by means of high-pressure carbon dioxide extraction, because of the similar solution behavior of these substances.

As with natural products, the polymer mixtures examined likewise exhibit pronounced lipophilic behavior, given their good solubility in hexane or, in the case of some polymers, even complete miscibility with hexane. A person skilled in the art would therefore have to assume that mixtures of substances which consist predominantly of lipophilic components and have lipophilic properties (are soluble in hexane, for example) cannot be further separated into their individual constituents or components by means of high-pressure carbon dioxide extraction.

Surprisingly, however, separation of monomers or auxiliaries from the prepolymer by means of high-pressure carbon dioxide extraction has been found to be possible.

Tests have shown that, for example, monomers, acrylates and methacrylates, aldehydes, dioxanes and low-molecular weight cyclic esters, as well as diisocyanates (TDI, MDI, HDI, IPDI, H12MDI, etc.), can be separated from the prepolymerizate virtually without residue.

In addition, it has been found that even troublesome oligomeric synthesis constituents which adversely affect the physical properties of certain polymers, for example, can be removed jointly with the above-mentioned monomers.

Especially surprisingly, it has been shown that, in a process according to the dependent claims in particular, selective separation of the monomers concerned can be obtained at high purity.

The carbon dioxide is preferably used in its thermodynamic state above its critical pressure and above its critical temperature. The critical pressure of carbon dioxide is 73.8 bar, and the critical temperature is 31.06° C. Above the critical pressure and the critical temperature, the dissolving power of carbon dioxide is especially high for the monomers or auxiliaries to be extracted.

In order to take full advantage of the increased dissolving power of carbon dioxide's supercritical pressure and temperature, a process is preferred in which the prepolymer and the solvent, pure dry carbon dioxide with a moisture content under 20 ppm, are brought together at pressures between 100 bar and 320 bar. Correspondingly, a process is preferred in which the prepolymer and the solvent are brought together at temperatures between 40° C. and 80° C. The increased dissolving power of carbon dioxide already exists in the selected temperature range, but the risk of cracking of the substances contained in the prepolymer is not yet present.

Drying of the commercially available $CO_2$ takes place in that for drying the gaseous $CO_2$ is cooled to a dew point <−50° C. at equilibrium pressure, for example to −70° C. at 14.5 bar, and is then passed through si[li]ca gel or a molecular sieve. The dried $CO_2$ so obtained, with a moisture content under 20 ppm, is then liquefied and then may be reacted with the prepolymer.

Additionally preferred is a process in which the monomers dissolved in the carbon dioxide are separated from the prepolymer together with the carbon dioxide after the carbon dioxide has first been brought into contact with the prepolymer to initiate the extraction process. Separation of the carbon dioxide with the monomers dissolved therein from the prepolymer may be effected in that, for example, the carbon dioxide enriched with monomers is drawn off, while at the same time, pure carbon dioxide is supplied, so that finally the purified prepolymer is found in a carbon dioxide atmosphere. There, the carbon dioxide acts as protective gas and prevents the purified prepolymer and the monomers from coming into contact with moisture or acid.

In the preferred process, the monomers dissolved in the carbon dioxide are removed after the carbon dioxide with the dissolved monomers has been separated from the prepolymer. In this way, essentially pure carbon dioxide as well as essentially pure monomers, which can then be reused, may be recovered.

Separation of the monomers is advantageously carried out at pressures between 20 and 80 bar. At the same time, the temperature advantageously is in a range between −10° C. and +40° C. At these pressures and temperatures, the carbon dioxide has a considerably lower dissolving power for the monomers than at the preferred extraction pressures and temperatures, so that the monomers originally dissolved separate out of the carbon dioxide. The separated monomers are advantageously used again for purposes of synthesis. After separation of the monomers, the carbon dioxide is likewise reused for extracting additional monomers.

Bringing together of prepolymer and solvent and removal of carbon dioxide with the monomers dissolved therein is advantageously carried out continuously. For this, the solvent with the carbon dioxide and the prepolymer are advantageously carried past one another in a counterflow process in such fashion that they have as great as possible a surface area for contact with one another, so that an efficient extraction process is produced, which permits a high throughput.

Separation of the monomers from the carbon dioxide also is advantageously carried out continuously. The carbon dioxide thereby recovered may be returned for further extraction, while the recovered monomer may be returned to the synthesis stage of the prepolymer preceding extraction. In this way, closed circuits are obtained for the carbon dioxide as well as for the monomers, so that only energy must be consumed continuously for separating the organic monomers which are used in synthesizing organic polymers or take part in the polymerization reaction and are still contained in the prepolymer. The solvent and the extracted substances are recirculated. Solvent need not be added continuously, nor do waste products to be disposed of accumulate continuously.

The invention therefore permits very low-cost and environmentally sound separation of organic monomers or auxiliaries which are used in synthesizing organic polymers or take part in a polymerization reaction and are still contained in the prepolymer (polymer). For extraction, the prepolymer to be purified should advantageously be present in liquid or viscous form.

In a preferred process, isocyanates are separated from the prepolymer.

Likewise preferred is a process in which aldehydes, dioxanes, cyclic esters and/or glycols are separated from the prepolymer.

In a preferred alternative of the process, acrylic esters and/or methacrylic esters are separated from the prepolymer.

Alternatively preferred is a process in which process-dependent vehicles, in particular starters, diluents or stabilizers, are separated from the prepolymer.

The process will now be explained in detail by means of several examples.

BRIEF DESCRIPTION OF THE DRAWING

The FIGURE shows a schematic representation of an apparatus for high-pressure extraction.

In the apparatus for high-pressure extraction, a receiving tank 10, a first heat exchanger 12, a flowmeter 14, a metering pump 16, a separating column 18 and a discharge valve 20 are connected in series.

In the tank 10 is found the prepolymer for synthesizing an organic [polymer] with the monomers or auxiliaries contained therein, i.e., a mixture of polymers and monomers. This mixture goes from the tank 10 into the heat exchanger 12, where its temperature is adjusted so that the mixture has a viscosity suitable for extraction. The mixture then flows through the flowmeter 14 and is fed by the pump 16 to the separating column 18.

Extraction takes place in the column 18. The purified prepolymer of the polymer synthesis (the polymer) may be discharged as raffinate through the bottom discharge valve 20 of the separating column 18.

For extraction, pure solvent, i.e., pure dry carbon dioxide with a moisture content under 20 ppm, is continuously fed to the column 18. The inlet for the solvent is located in the bottom region of the separating column, while the inlet for the mixture is in the upper region of the column. On the other hand, the discharge for the purified polymer is in the bottom region of the separating column and the discharge for the solvent with the monomers dissolved therein is located in the upper region of the separating column, so that the column is traversed by the polymer and the solvent in counterflow. This contributes to effective extraction. In addition, the separating column 18 is designed so that the polymer and the solvent have as great as possible a surface area for contact with one another within the column.

The extraction pressure $P_E$ and the extraction temperature $T_E$ in the separating column advantageously are selected so that the carbon dioxide is in its supercritical thermodynamic state with respect to pressure as well as with respect to temperature. The dissolving power of the carbon dioxide for the monomers or auxiliaries to be extracted is especially high in this state.

For the solvent circuit, the apparatus has a first pressure-control valve 22, a separator 24, a second pressure-control valve 26, a circuit valve 28, a carbon dioxide liquefier 30, a carbon dioxide collector 32, a liquid carbon dioxide pump 34, a carbon dioxide flowmeter 36 and a second heat exchanger 38, in addition to the separating column 18 already described. By means of the liquid carbon dioxide pump 34, first carbon dioxide is delivered from the carbon dioxide collector 32 and through the second heat exchanger 38, in which the carbon dioxide is brought to the extraction temperature $T_E$, into the separating column 18 until the extraction pressure $P_E$ prevails there.

Once the extraction pressure $P_E$ has been reached, the first pressure-control valve 22 opens and the solvent (carbon dioxide) with the monomers dissolved therein is able to leave the separating column through the first pressure-control valve 22. In so doing, only as much solvent as is delivered by the liquid carbon dioxide pump 34 comes out of the column 18. Accordingly, a constant extraction pressure $P_E$ is produced at a continuous carbon dioxide throughput.

In the first pressure-control valve 22, the solvent leaving the separating column 18 is expanded to a lower pressure, the separating pressure $P_A$, and then goes into the heatable separating tank 24. First, the separating pressure $P_A$ builds up there. Once this has been reached, the second pressure-control value 26 opens and subsequently keeps the separating pressure $P_A$ constant.

The separator is operated within a temperature and pressure range in which the dissolving power of the monomer or auxiliaries is considerably reduced with respect to the temperatures and pressures prevailing in the separating column 18. As a result, the monomers or auxiliaries in the separator settle out of the solvent quantitatively and may be carried out through the bottom valve 40 of the separator as extract and then returned to the synthesis reactor (not illustrated).

The purified solvent $CO_2$ flows out of the separator 24 through the second pressure-control valve 26 and the circuit valve 28 to the carbon dioxide liquefier 30.

The carbon dioxide is liquefied in the liquefier 30 and is then collected in the collector 32. From there, the liquid carbon dioxide is delivered by the liquid carbon dioxide pump 34 through the carbon dioxide flowmeter 36 and the second heat exchanger 38 back into the separating column 18. The circuit for the solvent is thereby closed.

The carbon dioxide is brought to the required extraction temperature in the second heat exchanger.

The extraction pressure $P_E$ is held in the pressure column 18 by means of the first pressure-control valve 22.

Correspondingly, the required pressure $P_A$ is held in the separator 24 by the second pressure-control valve 26.

To introduce dry carbon dioxide into the solvent circuit, the carbon dioxide, with circuit valve 28 closed, is delivered from a carbon dioxide tank, not illustrated, through a feed valve 42 and a molecular sieve filter 44, as well as through a second feed valve 46 and the carbon dioxide liquefier 30, into the collector 32. As soon as the process parameters have become established, the first feed valve 42, 46 is closed and the circuit valve 28 is opened.

The molecular sieve filter advantageously has a pore diameter of around 4 Å.

The essential process parameters are the extraction pressure $P_E$[bar] and the extraction temperature $T_E$[° C.] in the separating column 18, as well as the separating pressure $P_A$[bar] and the separating temperature $T_A$[° C.] in the separator. Another process parameter is the ratio of the mass flows of carbon dioxide and raw material, i.e., the prepolymer. In the following, this ratio is called the throughput coefficient.

TABLE 1

| Pressure P [bar] | | Temperature ° C. | | | | |
|---|---|---|---|---|---|---|
| | | 40 | 50 | 60 | 70 | 80 |
| 100 | Density $CO_2$ [g/cm³] | 0.68 | 0.45 | 0.31 | 0.26 | 0.23 |
| 150 | Density $CO_2$ [g/cm³] | 0.80 | 0.73 | 0.63 | 0.54 | 0.45 |
| 200 | Density $CO_2$ [g/cm³] | 0.85 | 0.80 | 0.74 | 0.68 | 0.61 |
| 250 | Density $CO_2$ [g/cm³] | 0.89 | 0.85 | 0.80 | 0.75 | 0.70 |
| 300 | Density $CO_2$ [g/cm³] | 0.92 | 0..88 | 0.84 | 0.80 | 0.76 |

The density of dry carbon dioxide, with a moisture content of about 2.5 ppm, at various temperatures and pressures at which the process according to the invention works depending upon the type of monomers, is listed in Table 1. For extraction, preferred parameter pairs of extraction pressure $P_E$ and extraction temperature $T_E$ are identified in the table in that the corresponding pairs for carbon dioxide density are shown in bold face. Thus, Table 1 shows that, at an extraction pressure of 150 bar, extraction temperatures between 50° C. and 60° C. are especially favorable, the carbon dioxide having a density between 0.63 g/cm³ and 0.73 g/cm³. At an extraction pressure of 200 bar, the preferred extraction temperature is between 50° C. and 70° C., and the density of the carbon dioxide is between 0.68 g/cm³ and 0.8 g/cm³. At an extraction pressure of 250 bar, an extraction temperature between 70° C. and 80° C. and a corresponding carbon dioxide density between 0.7 g/cm³ and 0.75 g/cm³ are preferred. At an extraction pressure of 300 bar, the extraction temperature should be in the vicinity of 80° C., which corresponds to a density of the carbon dioxide of 0.76 g/cm³.

Favorable process parameters for the separator are a separating pressure $P_A$ of 55 bar and a separating temperature $T_A$ of 30° C. The density of the carbon dioxide is then 0.15 g/cm³.

Some examples of extractions carried out follow below.

EXAMPLE 1

Polyurethane

Starting materials were polyurethane prepolymers obtained by synthesis, HDI (hexamethylene-1,6-diisocyanate) contained as monomer. The prepolymer obtained by synthesis contained polymers and monomers (HDI) and was then purified with dried $CO_2$ by the process according to the invention, in order to separate the monomers (HDI).

| Process parameters: | |
|---|---|
| Solvent: | Dried $CO_2$ (moisture content: 2.5 ppm) |
| Extraction pressure $P_E$ | $P_E$ = 200 bar |
| Extraction temperature $T_E$ | $T_E$ = 60° C. |
| Density $CO_2$, at $P_E/T_E$ | = 0.74 g/cm³ |
| Separating pressure $P_A$ | $P_A$ = 55 bar |
| Separating temperature $T_A$ | $T_A$ = 30° C. |

-continued

Process parameters:

| Solvent: | Dried $CO_2$ (moisture content: 2.5 ppm) |
|---|---|
| Density $CO_2$, at $P_A/T_A$ | $= 0.15$ g/cm$^3$ |
| Throughput coefficient | $= 8$ kg $CO_2$/h |
| | 1 kg prepolymer/h |

Result

TABLE 2

| Composition of prepolymer before $CO_2$ treatment | Composition of prepolymer after $CO_2$ treatment | Purity of monomer obtained by $CO_2$ treatment |
|---|---|---|
| 800 g polymer | 799.50 g polymer | 199.50 g monomer (HDI) |
| 200 g monomer (HDI) | 0 g monomer (HDI)* | Purity: 99.80% |
| 900 g polymer | 898.80 g polymer | 99.50 g monomer |
| 100 g monomer (HDI) | 0 g monomer (HDI)* | Purity: 99.75% |
| 950 g polymer | 948.10 g polymer | 49.85 g monomer |
| 50 g monomer (HDI) | 0 g monomer (HDI)* | Purity: 99.90% |
| 980 g polymer | 978.8 g polymer | 19.95 g monomer |
| 20 g monomer (HDI) | 0 g monomer (HDI)* | Purity: 99.75% |
| 990 g polymer | 989.5 g polymer | 9.80 g monomer |
| 10 g monomer (HDI) | 0 g monomer (HDI)* | Purity: 99.95% |

*Monomer no longer detectable

EXAMPLE 2

Acrylic

Starting materials were acrylic prepolymers obtained by synthesis, containing ETAC (ethyl acetate) contained as solvent and monomer. The prepolymer obtained by synthesis contained polymers and monomers and was then purified with dried $CO_2$ according to the process according to the invention, in order to separate the monomers.

Process parameters:

| Solvent: | Dried $CO_2$ (moisture content: 2.5 ppm) |
|---|---|
| Extraction pressure $P_E$ | $P_E = 250$ bar |
| Extraction temperature $T_E$ | $T_E = 70°$ C. |
| Density $CO_2$, at $P_E/T_E$ | $= 0.75$ g/cm$^3$ |
| Separating pressure $P_A$ | $P_A = 55$ bar |
| Separating temperature $T_A$ | $T_A = 30°$ C. |
| Density $CO_2$, at $P_A/T_A$ | $= 0.15$ g/cm$^3$ |
| Throughput coefficient | $= 7.5$ kg $CO_2$/h |
| | 1 kg prepolymer/h |

Result

TABLE 3

| Composition of prepolymer before $CO_2$ treatment | Composition of prepolymer after $CO_2$ treatment | Purity of monomer obtained by $CO_2$ treatment |
|---|---|---|
| 950 g polymer | 949.50 g polymer | 49.80 g monomer |
| 50 g monomer | 4 g monomer | Purity: 99.56% |
| 960 g polymner | 959.80 g polymer | 39.96 g monomer |
| 40 g monomer | 0 g monomer * | Purity: 99.53% |
| 970 g polymer | 969.70 g polymer | 29.95 g monomer |
| 30 g monomer | 0 g monomer * | Purity: 99.9% |
| 980 g polymer | 979.70 g polymer | 19.89 g monomer |
| 20 g monomer | 0 g monomer * | Purity: 99.80% |

* Monomer np longer detectable

EXAMPLE 3

Polyester diols

Starting materials were polyester diol prepolymers obtained by synthesis, dioxane used as monomer. The prepolymer obtained by synthesis contained polymers and monomers (dioxane) and was then purified with dried $CO_2$ by to the process according to the invention, in order to separate the monomers (dioxane). The object was to produce an odorless end product.

Process parameters:

| Solvent: | Dried $CO_2$ (moisture content: 2.5 ppm) |
|---|---|
| Extraction pressure $P_E$ | $P_E = 150$ bar |
| Extraction temperature $T_E$ | $T_E = 50°$ C. |
| Density $CO_2$, at $P_E/T_E$ | $= 0.73$ g/cm$^3$ |
| Separating pressure $P_A$ | $P_A = 55$ bar |
| Separating temperature $T_A$ | $T_A = 30°$ C. |
| Density $CO_2$, at $P_A/T_A$ | $= 0.15$ g/cm$^3$ |
| Throughput coefficient | $= 9$ kg $CO_2$/h |
| | 1 kg prepolymer/h |

Result

TABLE 4

| Composition of prepolymer before $CO_2$ treatment | Composition of prepolymer after $CO_2$ treatment. | Purity of monomer obtained by $CO_2$ treatment |
|---|---|---|
| 950 g polymer | 949.80 g polymer | 49.89 g monomer (dioxane) |
| 50 g monomer (dioxane) | 0 g monomer (dioxane)* | Purity: 99.85% |
| 990 g polymer | 989.75 g polymer | 9.95 g monomer (dioxane) |
| 10 g monomer (dioxane) | 0 g monomer (dioxane)* | Purity: 99.79% |

*Monomer no longer detectable

EXAMPLE 4

THF and MEK (tetrahydrofuran and methyl ethyl ketone) were used as vehicles for synthesizing polymers. The prepolymer obtained by synthesis contained polymers and vehicle (THF, MEK) and was then purified with $CO_2$ by the process according to the invention, in order to separate the vehicles (THF, MEK).

Process parameters:

| Solvent: | Dried $CO_2$ (moisture content: 2.5 ppm) |
|---|---|
| Extraction pressure $P_E$ | $P_E = 250$ bar |
| Extraction temperature $T_E$ | $T_E = 70°$ C. |

-continued

Process parameters:

| Solvent: | Dried $CO_2$ (moisture content: 2.5 ppm) |
|---|---|
| Density $CO_2$, at $P_E/T_E$ | = 0.74 g/cm³ |
| Separating pressure $P_A$ | $P_A$ = 55 bar |
| Separating temperature $T_A$ | $T_A$ = 30° C. |
| Density $CO_2$, at $P_A/T_A$ | = 0.15 g/cm³ |
| Throughput coefficient | = 5 kg $CO_2$/h |
| | 1 kg prepolymer/h |

Result

TABLE 5

| Composition of prepolymer before $CO_2$ treatment | Composition of prepolymer after $CO_2$ treatment | Purity of monomer obtained by $CO_2$ treatment |
|---|---|---|
| 800 g polymer | 799.50 g polymer | 199.85 g monomer (THF) |
| 200 g monomer (THF) | 0 g monomer (THF)* | Purity: 99.85% |
| 900 g polymer | 899.10 g polymer | 99.85 g monomer (MEK) |
| 100 g monomer (MEK) | 0 g monomer (MEK)* | Purity: 99.793% |
| 970 g polymer | 969.89 g polymer | 29.85 g monomer (THF) |
| 30 g monomer (THF) | 0 g monomer (THF)* | Purity: 99.35% |
| 980 g polymer | 979.10 g polymer | 19.79 g monomer (MEK) |
| 20 g monomer (MEK) | 0 g monomer (MEK)* | Purity: 99.40% |

* Monomer no longer detectable

The test results listed in Examples 1 to 4 illustrate the results obtainable by the process for separating organic monomers or auxiliaries which are used in synthesizing organic polymers or take part in the polymerization reaction and are still contained in the prepolymer (polymer).

In order to demonstrate the effectiveness of the process according to the invention, a comparative test was performed: The test was carried out according to Example 1 where $CO_2$ with a moisture content of 70 ppm was used as solvent. The purity of the HDI (hexamethylene-1,6-diisocyanate) monomer recovered by the $CO_2$ treatment was measured to be 91%.

Comparative Test

Starting materials were polyurethane prepolymers obtained by synthesis, HDI (hexamethylene-1,6-diisocyanate) contained as monomer. The prepolymer obtained by synthesis contained polymers and monomers (HDI) and was then purified with undried $CO_2$ (with a moisture content of 70 ppm), in order to separate the monomers (HDI).

Process parameters:

| Solvent: | Undried $CO_2$ (moisture content: 70 ppm) |
|---|---|
| Extraction pressure $P_E$ | $P_E$ = 200 bar |
| Extraction temperature $T_E$ | $T_E$ = 60° C. |
| Density $CO_2$, at $P_E/T_E$ | = 0.74 g/cm³ |
| Separating pressure $P_A$ | $P_A$ = 55 bar |
| Separating temperature $T_A$ | $T_A$ = 30° C. |
| Density $CO_2$, at $P_A/T_A$ | = 0.15 g/cm³ |

Result

The monomer (HDI) obtained by the $CO_2$ treatment had a purity of 91%.

What is claimed is:

1. Process for separating organic monomers or auxiliaries, which are used in synthesizing organic polymers or take part in a polymerization reaction, from a prepolymer obtained by the synthesis, whereby the monomers or auxiliaries are extracted from the prepolymer by use of compressed carbon dioxide as a solvent, and whereby the carbon dioxide is used in its thermodynamic state above its critical pressure and above its critical temperature, the improvement comprising carbon dioxide being dried to a moisture content under 20 ppm before it is brought together with the prepolymer.

2. Process according to claim 1, wherein the carbon dioxide is dried to a moisture content under 2.5 ppm.

3. Process according to claim 1 or 2, wherein the prepolymer and the dried carbon dioxide are brought together at pressures between 150 bar and 300 bar.

4. Process according to claim 1 or 2, wherein the prepolymer and the dried carbon dioxide are brought together at temperatures between 40° C. and 80° C.

5. Process according to claim 1 or 2, wherein, for drying, the carbon dioxide is passed through a molecular sieve or silica gel before extraction.

6. Process according to claim 1 or 2, wherein, for drying, the gaseous carbon dioxide is cooled to a dew point <−50° C. at equilibrium pressure and is then passed through silica gel or a molecular sieve.

7. Process according to claim 1 or 2, wherein the monomers dissolved in the dried carbon dioxide are separated from the prepolymer together with the carbon dioxide.

8. Process according to claim 7, wherein the monomers dissolved in the dried carbon dioxide are separated after the carbon dioxide has been separated from the prepolymer with the dissolved monomers.

9. Process according to claim 8, wherein separation of the monomers is carried out at pressures between 20 and 80 bar.

10. Process according to claim 8, wherein separation of the monomers is carried out at temperatures between −10° C. and +40° C.

11. Process according to claim 8, wherein the separated monomers are reused for purposes of synthesis.

12. Process according to claim 1 or 2, wherein, after separation of the monomers, the dried carbon dioxide is reused for separating additional monomers.

13. Process according to claim 1 or 2, wherein bringing prepolymers and dried carbon dioxide together and removing carbon dioxide with the monomers dissolved therein is carried out continuously.

14. Process according to claim 1 or 2, wherein the monomers are separated from liquid or viscous prepolymers.

15. Process according to claim 1 or 2, wherein isocyanates are separated from the prepolymer.

16. Process according to claim 1 or 2, wherein aldehydes, dioxanes, cyclic esters and/or glycols are separated from the prepolymer.

17. Process according to claim 1 or 2, wherein acrylic esters and/or methacrylic esters are separated from the prepolymer.

18. Process according to claim 1 or 2, wherein added process-dependent vehicles, are separated from the prepolymer.

* * * * *